(12) United States Patent
Kilgore et al.

(10) Patent No.: US 10,196,328 B2
(45) Date of Patent: Feb. 5, 2019

(54) CATALYST SYSTEMS AND ETHYLENE OLIGOMERIZATION METHOD

(71) Applicant: Chevron Phillips Chemical Company LP, The Woodlands, TX (US)

(72) Inventors: Uriah J. Kilgore, Kingwood, TX (US); Steven M. Bischof, Humble, TX (US); Orson L. Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 182 days.

(21) Appl. No.: 15/171,170

(22) Filed: Jun. 2, 2016

(65) Prior Publication Data
US 2017/0349505 A1 Dec. 7, 2017

(51) Int. Cl.
| | |
|---|---|
| *C07C 2/32* | (2006.01) |
| *B01J 31/18* | (2006.01) |
| *B01J 31/14* | (2006.01) |
| *B01J 31/22* | (2006.01) |
| *B01J 31/24* | (2006.01) |
| *C07C 2/36* | (2006.01) |

(52) U.S. Cl.
CPC ............... *C07C 2/32* (2013.01); *B01J 31/143* (2013.01); *B01J 31/189* (2013.01); *B01J 31/2295* (2013.01); *B01J 31/24* (2013.01); *C07C 2/36* (2013.01); *B01J 2231/20* (2013.01); *B01J 2531/62* (2013.01); *C07C 2531/22* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 6,046,211 A | 4/2000 | Hansen, Jr. et al. | |
| 8,680,003 B2 | 3/2014 | Sydora et al. | |
| 8,865,610 B2 | 10/2014 | Sydora et al. | |
| 9,283,555 B2 | 3/2016 | Sydora et al. | |
| 9,732,106 B2 | 8/2017 | Sydora et al. | |
| 2007/0149582 A1 | 6/2007 | Kordes et al. | |
| 2012/0309965 A1 | 12/2012 | Sydora et al. | |
| 2013/0331629 A1 | 12/2013 | Sydora et al. | |
| 2016/0375431 A1* | 12/2016 | Carney .................... | C07F 9/46 585/513 |

FOREIGN PATENT DOCUMENTS

| | | |
|---|---|---|
| WO | 2011/082192 A1 | 7/2011 |
| WO | 2013184579 A1 | 12/2013 |
| WO | 2017209959 A1 | 12/2017 |

OTHER PUBLICATIONS

"Group notation revised in periodic table," Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Foreign communication from a related counterpart application—International Search Report and Written Opinion, PCT/US2017/033162, dated Jun. 30, 2017, 10 pages.
McGuinness, D. S., et al., "Novel CR-PNP complexes as catalysts for the trimerisation of ethylene," Chemical Communications—CHEMCOM, Jan. 1, 2003, pp. 334-335, The Royal Society of Chemistry.
Gong, D., et al., "Ethylene polymerization by PN3-type pincer chromium(III) complexes," Journal of Molecular Catalysis A: Chemical, 2014, pp. 100-107, vol. 395, Elsevier B. V.
Braunstein, Pierre, et. al. "Synthesis of Nickel Phenyl Complexes with New Chelating κ2-P,N Ligands Derived from α-Iminoazatriphenylphosphoranes. [Erratum to document cited in CA127:17791]," Journal of Organometallic Chemistry, 1999, vol. 582, p. 370, Elsevier Science S.A.
Braunstein, Pierre, et. al. "Synthesis of Nickel Phenyl Complexes with New Chelating κ2-P,N Ligands Derived from α-Iminoazatriphenylphosphoranes," Journal of Organometallic Chemistry, 1999, vol. 582, pp. 371-377, Elsevier Science S.A.
Braunstein, Pierre, et. al., "Synthesis of Nickel Phenyl Complexes with New Chelating κ2-P,N Ligands Derived from α-Iminoazatriphenylphosphoranes," Journal of Organometallic Chemistry, 1997, vol. 529, pp. 387-393, Elsevier Science S.A.
Dyer, Philip W., et al.,"Rigid N-Phosphino Guanidine P,N Ligands and Their Use in Nickel-Catalyzed Ethylene Oligomerization," Organometallics, 2008, vol. 27, pp. 5082-5087, American Chemical Society.
Voß, Corinna, et al., Intramolecular d10-d10 interactions in neutral, Binuclear Au(I) complexes supported by amino-thiazoline- and -thiazole-based P,N-phosphine ligands, C.R. Chimie, vol. 15, 2012, pp. 229-236, Elsevier Masson SAS.
Zhang, Shuanming, et al., "Reactions of a Phosphinoimino-thiazoline-Based Metalloligand with Organic and Inorganic Electrophiles and Metal-Induced Ligand Rearrangements," Organometallics, 2010, vol. 29, pp. 6660-6667, American Chemical Society.
Filing receipt and specification for patent application entitled "Catalyst Systems and Ethylene Oligomerization Method," by Uriah J. Kilgore, et al., filed Dec. 1, 2017 as U.S. Appl. No. 15/828,921.
Buckley, G. D., et al., "Aliphatic Nitro-compounds. Part XV. Preparation of Heterocyclic Bases by Reduction of 3-Nitroalkyl Cyanides," 1947, pp. 1508-1511, Imperial Chemical Industries Limited, Research Laboratories, United Kingdom.
Shankaran, K, et al., "Evaluation of pyrrolidin-2-imines and 1,3-thiazolidin-2-imines as inhibitors of nitric oxide synthase," Bioorganic & Medicinal Chemistry Letters, 2004, pp. 4539-4544, vol. 14, Elsevier Ltd.

* cited by examiner

*Primary Examiner* — Yun Qian
(74) *Attorney, Agent, or Firm* — Conley Rose, P.C.

(57) ABSTRACT

A catalyst system comprising i) a 2-[(phosphinyl)aminyl] cyclic imine transition metal compound complex and ii) an organoaluminum compound. A process comprising contacting i) ethylene, ii) a catalyst system comprising (a) a 2-[(phosphinyl)aminyl] cyclic imine transition metal compound complex, and (b) an organoaluminum compound, and iii) optionally hydrogen to form an oligomer product.

18 Claims, No Drawings

CATALYST SYSTEMS AND ETHYLENE OLIGOMERIZATION METHOD

CROSS-REFERENCE TO RELATED APPLICATIONS

Not applicable.

FIELD

The present disclosure relates to processes for producing ethylene oligomers. More particularly, the present disclosure relates to improved catalyst systems and processes for oligomerizing ethylene.

BACKGROUND

Olefins, also commonly known as alkenes, are important items of commerce. Their many applications include employment as intermediates in the manufacture of detergents, as precursors to more environmentally-friendly refined oils, as monomers, and as precursors for many other types of products. An important subset of olefins are alpha olefins, and one process of making alpha olefins is via oligomerization of ethylene, which is a catalytic reaction involving various types of catalysts and/or catalyst systems. Examples of catalysts and catalyst systems used commercially to produce alpha olefins include alkylaluminum compounds, certain nickel-phosphine complexes, titanium halides with a Lewis acid (e.g., diethyl aluminum chloride), zirconium halides and/or zirconium alkoxides with alkylaluminum compounds. Additionally, there is a selective ethylene trimerization and/or tetramerization catalyst system for producing 1-hexene that uses a chromium containing compound (e.g., a chromium carboxylate), a nitrogen-containing ligand (e.g., a pyrrole), and a metal alkyl (e.g., alkyl aluminum compounds).

Several non-commercial oligomerization catalyst systems to produce alpha olefins are based upon metal complexes of pyridine bis-imines, metal complexes of α-diimine compounds having a metal complexing group, and selective trimerization and/or tetramerization catalyst systems using a metal compound (e.g., a chromium compound) complex of a diphosphinylamine, phosphinyl formamidine, phosphinyl amidine, or phosphinyl guanidine. These catalyst systems typically use an organoaluminum compound (e.g., aluminoxane) as a component of the catalyst systems for olefin oligomerization.

Applications and demand for olefins (e.g., alpha olefins) continue to multiply, and competition to supply them correspondingly intensifies. Thus, additional novel and improved catalyst systems and processes for olefin oligomerization are desirable.

SUMMARY

Disclosed herein are catalyst systems comprising i) a 2-[(phosphinyl)aminyl] cyclic imine transition metal compound complex and ii) an organoaluminum compound.

Also disclosed herein is a process comprising contacting i) ethylene, ii) a catalyst system comprising (a) a 2-[(phosphinyl)aminyl] cyclic imine transition metal compound complex, and (b) an organoaluminum compound, and iii) optionally hydrogen to form an oligomer product.

DETAILED DESCRIPTION

In the description herein, various ranges and/or numerical limitations can be expressly stated. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can be used interchangeably and can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or process steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or process to which the term is applied. For example, a feedstock consisting essentially of a material A can include impurities typically present in a commercially produced or commercially available sample of material A. When a claim includes different features and/or feature classes (for example, a process step, feedstock features, and/or product features, among other possibilities), the transitional terms comprising, consisting essentially of, and consisting of apply only to the feature class that is utilized and it is possible to have different transitional terms or phrases utilized with different features within a claim. For example a process can comprise several recited steps (and other non-recited steps) but utilize a catalyst system preparation consisting of specific steps and/or can utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and processes are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Unless otherwise indicated, the definitions set forth herein are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon-carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the processes described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in a 2-[(phosphinyl)aminyl] cyclic imine can be an inert functional group because a single metal compound cannot complex with both the para ether group and the two nitrogen atoms of the 2-[(phosphinyl)aminyl] cyclic imine group in a single metal compound complex molecule. Thus, the inertness of a particular functional group is not only related to the functional group's inherent inability to complex the metal compound but can also be related to the functional group's position within the metal compound complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and can include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a cyclic and acyclic, and/or linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction zone effluent," and its derivatives generally refers to all materials which exit the reaction and can include reaction system feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction system through the reaction zone outlet/discharge, a reaction zone oligomer product effluent refers to only the oligomer product within the reaction zone effluent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the features disclosed herein. Features within this disclosure that are provided as maximum values can be alternatively stated as "less than or equal to" any recited maximum value for the feature disclosed herein.

Within this disclosure the normal rules of organic chemistry nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

As used herein, a 2-[(phosphinyl)aminyl] cyclic imine is an imine compound (i.e., a compound having a non-aromatic carbon-nitrogen double bond) where the carbon atom and the nitrogen atom are contained within a ring or a ring system and having a phosphinylaminyl group located on the carbon atom of the imine carbon-nitrogen double bond. As such, a "2-[(phosphinyl)aminyl] cyclic imine transition metal compound complex" and its derivations is a complex between a transition metal compound and a 2-[(phosphinyl) aminyl] cyclic imine.

Use of the term "optionally" with respect to any element of a claim is intended to mean that the subject element can be required, or alternatively, may not be required. Both alternatives are intended to be within the scope of the claim.

Processes and/or methods described herein can utilize steps, features, and compounds which are independently described herein. The process and/or methods described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes and/or methods described herein can have multiple steps, features (e.g. reagent ratios, formation conditions, among other considerations), and/or multiple compounds and/or compositions using no descriptor or sometimes having the same general identifier. Consequently, it should be noted that the processes and/or methods described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Processes of forming oligomer products are described herein. Such processes generally comprise contacting ethylene and a catalyst system to form an oligomer product under oligomerization conditions. As used herein, the term "oligomerization" and its derivatives, refers to processes which produce a mixture of products containing at least 70 weight percent products containing from 2 to 30 ethylene units. Similarly, as used herein, an "oligomer" is a product that contains from 2 to 30 ethylene units while an "oligomer product" includes all products made by the process including the "oligomers" and products which are not "oligomers" (e.g., products which contain more than 30 monomer units). Further the terms "oligomer product" and "oligomerization product" can be used interchangeably.

As used herein, the term "trimerization," and it derivatives, refers to a process which produces a mixture of products containing at least 70 weight percent products containing three and only three ethylene units. As used herein, a "trimer" is a product which contains three and only three ethylene units while a "trimerization product" includes all products made by the trimerization process including the trimer and products which are not trimers (e.g. dimers or tetramers). Generally, a "trimerization" process using ethylene produces an oligomer product containing at least 70 weight percent hexene(s).

As used herein, the term "tetramerization," and its derivatives, refers to a process which produces a mixture of products containing at least 70 weight percent products containing four and only four ethylene units. As used herein, a "tetramer" is a product which contains four and only four ethylene units while a "tetramerization product" includes all products made by the tetramerization process including the tetramer and products which are not tetramers (e.g. dimers or trimer). Generally, a "tetramerization" process using ethylene produces an oligomer product containing at least 70 weight percent octene(s).

As used herein, the term "trimerization and tetramerization," and it derivatives, refers to a process which produces an oligomer product containing at least 70 weight percent products containing three and/or four and only three and/or four ethylene units. As used herein, a "trimerization and tetramerization product" includes all products made by the "trimerization and tetramerization" process including trimer, tetramer, and products which are not trimers or tetramers (e.g. dimers). Generally, a "trimerization and tetramerization" process using ethylene produces an oligomer product containing at least 70 weight percent hexene(s) and/or octene(s).

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

Aspects of this disclosure are directed to catalyst systems comprising i) a 2-[(phosphinyl)aminyl] cyclic imine transition metal compound complex, and ii) an organoaluminum compound. Generally, the 2-[(phosphinyl)aminyl] cyclic imine transition metal compound complex, the organoaluminum compound, any other catalyst system component(s) described herein, and any catalyst system component ratio(s) are independent elements of the catalyst systems. These catalyst system elements are independently described herein and can be utilized without limitation, and in any combination, to further describe catalyst systems utilized in aspects and/or embodiments described herein.

The 2-[(phosphinyl)aminyl] cyclic imine transition metal compound complexes utilized in the catalyst systems and/or the processes described herein can have general Structure APCITMC 1 or Structure APCITMC 2; alternatively, Structure APCITMC 1; or Structure APCITMC 2. In some embodiments, the 2-[(phosphinyl)aminyl] cyclic imine transition metal compound complexes utilized in the catalyst systems and/or the processes described herein can have Structure APCITMC 3, Structure APCITMC 4, Structure APCITMC 5, Structure APCITMC 6, Structure APCITMC 7, or Structure APCITMC 8; alternatively, Structure APCITMC 3, Structure APCITMC 5, or Structure APCITMC 7; alternatively, Structure APCITMC 4, Structure APCITMC 6, or Structure APCITMC 8; alternatively, Structure APCITMC 3 or Structure APCITMC 4; alternatively, Structure APCITMC 5 or Structure APCITMC 6; alternatively, Structure APCITMC 7 or Structure APCITMC 8; alternatively, Structure APCITMC 3; alternatively, Structure APCITMC 4; alternatively, Structure APCITMC 5; alternatively, Structure APCITMC 6; alternatively, Structure APCITMC 7; or alternatively, Structure APCITMC 8. In other embodiments, the 2-[(phosphinyl)aminyl] cyclic imine transition metal compound complexes utilized in the catalyst systems and/or the processes described herein can have Structure APCITMC 9, Structure APCITMC 10, Structure APCITMC 11, Structure APCITMC 12, Structure APCITMC 13, or Structure APCITMC 14; alternatively, Structure APCITMC 9, Structure APCITMC 11, or Structure APCITMC 13; alternatively, Structure APCITMC 10, Structure APCITMC 12, or Structure APCITMC 14; alternatively, Structure APCITMC 9 or Structure APCITMC 10; alternatively, Structure APCITMC 11 or Structure APCITMC 12; alternatively, Structure APCITMC 13 or Structure APCITMC 14; alternatively, Structure APCITMC 9; alternatively, Structure APCITMC 10; alternatively, Structure APCITMC 11; alternatively, Structure APCITMC 12; alternatively, Structure APCITMC 13; or alternatively, Structure APCITMC 14.

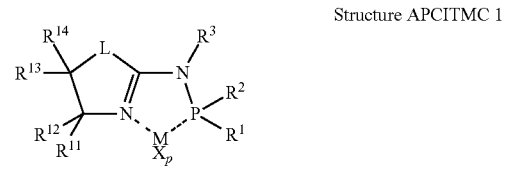

Structure APCITMC 1

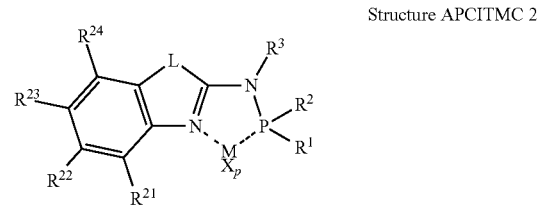

Structure APCITMC 2

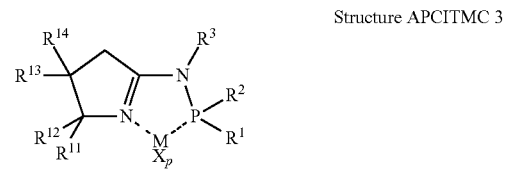

Structure APCITMC 3

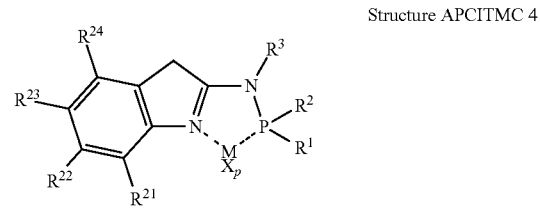

Structure APCITMC 4

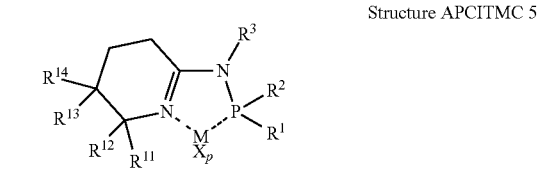

Structure APCITMC 5

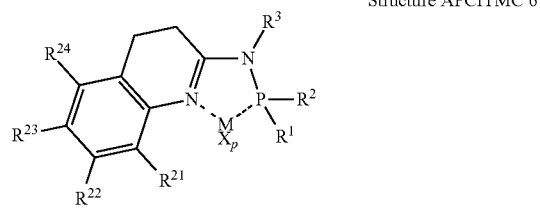

Structure APCITMC 6

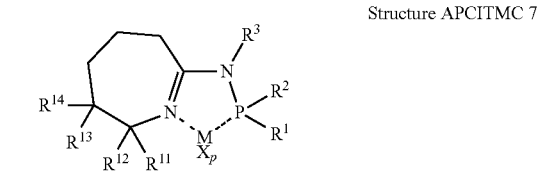

Structure APCITMC 7

Structure APCITMC 8

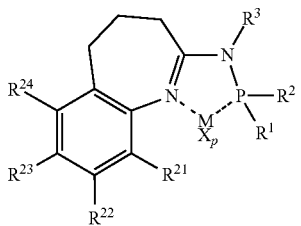

Structure APCITMC 9

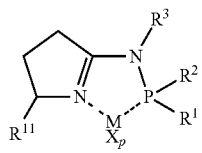

Structure APCITMC 10

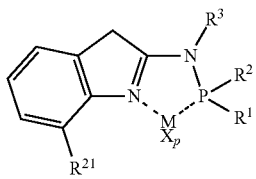

Structure APCITMC 11

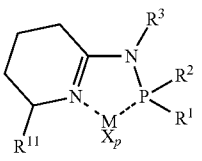

Structure APCITMC 12

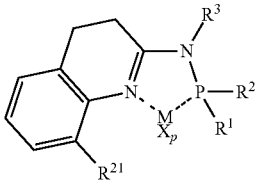

Structure APCITMC 13

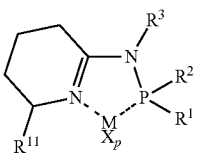

Structure APCITMC 14

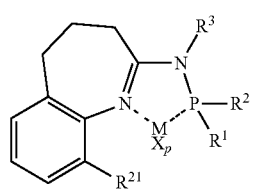

$R^1$, $R^2$, $R^3$, $R^{11}$, $R^{12}$, $R^{13}$, $R^{14}$, $R^{21}$, $R^{22}$, $R^{23}$, $R^{24}$, L and the transition metal compound $MX_p$ within the 2-[(phosphinyl)aminyl] cyclic imine transition metal compound complexes described herein are independent elements of the 2-[(phosphinyl)aminyl] cyclic imine transition metal compound complex structure in which they are present and are independently described herein. The independent descriptions of $R^1$, $R^2$, $R^3$, $R^{11}$, $R^{12}$, $R^{13}$, $R^{14}$, $R^{21}$, $R^{22}$, $R^{23}$, $R^{24}$, L and the transition metal compound $MX_p$ provided herein can be utilized without limitation, and in any combination, to further describe any 2-[(phosphinyl)aminyl] cyclic imine transition metal compound complex structure which have an $R^1$, $R^2$, $R^3$, $R^{11}$, $R^{12}$, $R^{13}$, $R^{14}$, $R^{21}$, $R^{22}$, $R^{23}$, $R^{24}$, L and/or the transition metal compound $MX_p$.

Generally, $R^1$ and/or $R^2$ of the 2-[(phosphinyl)aminyl] cyclic imine transition metal compound complexes independently can be an organyl group; alternatively, an organyl group consisting essentially of inert functional groups; or alternatively, a hydrocarbyl group. In an embodiment, the $R^1$ and/or $R^2$ organyl groups of the 2-[(phosphinyl)aminyl] cyclic imine transition metal compound complexes can be a $C_1$ to $C_{20}$, a $C_1$ to $C_{10}$, or a $C_1$ to $C_5$ organyl group. In an embodiment, the $R^1$ and/or $R^2$ organyl groups consisting of inert functional groups of the 2-[(phosphinyl)aminyl] cyclic imine transition metal compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ and/or $R^2$ hydrocarbyl groups of the 2-[(phosphinyl)aminyl] cyclic imine transition metal compound complexes independently can be a $C_1$ to $C_{20}$, a $C_1$ to $C_{15}$, a $C_1$ to $C_{10}$, or a $C_1$ to $C_5$ hydrocarbyl group. In further embodiments, the $R^1$ and $R^2$ organyl groups of the 2-[(phosphinyl)aminyl] cyclic imine transition metal compound complexes can be joined to form a ring or a ring system.

In an embodiment, $R^1$ and/or $R^2$ of any 2-[(phosphinyl)aminyl] cyclic imine transition metal compound complex can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ and/or $R^2$ of any 2-[(phosphinyl)aminyl] cyclic imine transition metal compound complex can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ and/or $R^2$ of any 2-[(phosphinyl)aminyl] cyclic imine transition metal compound complex independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^1$ and/or $R^2$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^1$ and/or $R^2$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^1$ and/or $R^2$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^1$ and/or $R^2$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^1$ and/or $R^2$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^1$ and/or $R^2$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^1$ and/or $R^2$ independently can be a $C_7$ to $C_{20}$, a $C_7$ to $C_{15}$, or a $C_7$ to $C_{10}$ aralkyl group. In any aspect or embodiment disclosed herein, each substituted aralkyl group which can be utilized as $R^1$ and/or $R^2$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$ and/or $R^2$.

In an embodiment, $R^1$ and/or $R^2$ independently can be a methyl group, an ethyl group, a propyl group, a butyl group, a pentyl group, a hexyl group, a heptyl group, or an octyl group. In some embodiments, $R^1$ and/or $R^2$ independently can be a methyl group, an ethyl group, an n-propyl (1-propyl) group, an iso-propyl (2-propyl) group, a iso-butyl (2-butyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a iso-butyl (2-butyl) group; alternatively, a tert-butyl (2-methyl-2-propyl) group; or alternatively, a neopentyl (2,2-dimethyl-1-propyl) group. In some embodiments, the alkyl groups which can be utilized as $R^1$ and/or $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$ and/or $R^2$ independently.

In an embodiment, $R^1$ and/or $R^2$ independently can be a cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for $R^1$ and/or $R^2$ can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; alternatively, a 2,6-disubstituted cyclohexyl group or a 2,5-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,5-disubstituted cyclopentyl group. In an embodiment where the substituted cycloalkyl group has more than one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^1$ and/or $R^2$.

In a non-limiting embodiment, $R^1$ and/or $R^2$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^1$ and/or $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, $R^1$ and/or $R^2$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^1$ and/or $R^2$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^1$ and/or $R^2$ independently can be a phenyl group, or a substituted phenyl group; alternatively, a phenyl group; or alternatively, a substituted phenyl group. In an embodiment, the substituted phenyl group, which can be utilized for $R^1$ and/or $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ and/or $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$ and/or $R^2$.

In a non-limiting embodiment, $R^1$ and/or $R^2$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Generally, the alkyl substituents of a dialkylphenyl group (general or specific) or trialkylphenyl group (general or specific) can be the same; or alternatively, the alkyl substituents of a dialkylphenyl group (general or specific) or trialkylphenyl group (general or specific) can be different. In some non-limiting embodiments, $R^1$ and/or $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^1$ and/or $R^2$ independently can be a phenyl group, a 2-alkoxyphenyl group, or a 4-alkoxyphenyl group. In some non-limiting embodiments, $R^1$ and/or $R^2$ independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^1$ and/or $R^2$ independently can be a phenyl group, a 2-halophenyl group, a 4-halophenyl group, or a 2, 6-dihalophenyl group. Generally, the halides of a dihalophenyl group can be the same; or alternatively, the halides of a dihalophenyl group can be different. In some embodiments, $R^1$ and/or $R^2$ independently can be a phenyl group, a 2-fluorophenyl group, a 4-fluorophenyl group, or a 2,6-difluorophenyl group.

In an embodiment, $R^1$ and/or $R^2$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^1$ and/or $R^2$.

Generally, $R^3$ of any 2-[(phosphinyl)aminyl] cyclic imine transition metal compound complex can be hydrogen or an organyl group; hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In an embodiment, the organyl group which can utilized as $R^3$ of the 2-[(phosphinyl) aminyl] cyclic imine transition metal compound complexes can be a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can utilized as $R^3$ of any 2-[(phosphinyl)aminyl] cyclic imine transition metal compound complex can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can utilized as $R^3$ of any 2-[(phosphinyl)aminyl] cyclic imine transition metal compound complex can be a $C_1$ to $C_{20}$, a $C_1$ to $C_{15}$, a $C_1$ to $C_{10}$, or a $C_1$ to $C_5$ hydrocarbyl group. In other embodiments, $R^3$ of any 2-[(phosphinyl)aminyl] cyclic imine transition metal compound complex can be a $C_1$ to $C_{20}$, a $C_1$ to $C_{15}$, a $C_1$ to $C_{10}$, or a $C_1$ to $C_5$ alkyl group. In yet other embodiments, $R^3$ of any 2-[(phosphinyl)aminyl] cyclic imine transition metal compound complex can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the 2-[(phosphinyl)aminyl] cyclic imine transition metal compound complexes.

Generally, $R^{11}$ of the 2-[(phosphinyl)aminyl] cyclic imine transition metal compound complexes having Structure APCITMC 1, Structure APCITMC 3, Structure APCITMC 5, Structure APCITMC 7, Structure APCITMC 9, Structure APCITMC 11, and/or Structure APCITMC 13 can be hydrogen or an organyl group; alternatively, hydrogen or an organyl group consisting essentially of inert functional groups; alternatively, hydrogen or a hydrocarbyl group; alternatively, an organyl group; alternatively, an organyl group consisting essentially of inert functional groups; alternatively, a hydrocarbyl group; or alternatively, hydrogen. In an embodiment, the organyl group which can be utilized as $R^{11}$ can be a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can be utilized as $R^{11}$ can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can be utilized as $R^{11}$ can be a $C_1$ to $C_{20}$, a $C_1$ to $C_{15}$, a $C_1$ to $C_{10}$, or a $C_1$ to $C_5$ hydrocarbyl group.

In an embodiment, $R^{11}$ of the 2-[(phosphinyl)aminyl] cyclic imine transition metal compound complexes having Structure APCITMC 1, Structure APCITMC 3, Structure APCITMC 5, Structure APCITMC 7, Structure APCITMC 9, Structure APCITMC 11, and/or Structure APCITMC 13, or any 2-[(phosphinyl)aminyl] cyclic imine transition metal compound complex having an $R^{11}$ group can be hydrogen, an alkyl group, or a substituted alkyl group; alternatively, hydrogen or an alkyl group; alternatively, hydrogen or a substituted alkyl group; alternatively, an alkyl group; alternatively, a substituted alkyl group; or alternatively, hydrogen. In any aspect or embodiment disclosed herein, the alkyl group which can be utilized as $R^{11}$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^{11}$ can be a $C_1$ to $C_{20}$, a $C_1$ to $C_{10}$, or $C_1$ to $C_5$ substituted alkyl group. In an embodiment, $R^{11}$ can be a methyl group, an ethyl group, a propyl group, a butyl group, a pentyl group, a hexyl group, a heptyl group, or an octyl group. In some embodiments, one or more of $R^{11}$ can be a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^{11}$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups (general or specific) can be utilized without limitation to further describe a substituted alkyl group which can be utilized as $R^{11}$.

Generally, $R^{12}$, $R^{13}$, and $R^{14}$ of the 2-[(phosphinyl)aminyl] cyclic imine transition metal compound complexes having Structure APCITMC 1, Structure APCITMC 3, Structure APCITMC 5, and/or Structure APCITMC 7, $R^{21}$ of the 2-[(phosphinyl)aminyl] cyclic imine transition metal compound complexes having Structure APCITMC 2, Structure APCITMC 4, Structure APCITMC 6, Structure APCITMC 8, Structure APCITMC 10, Structure APCITMC 12, and/or Structure APCITMC 14, and $R^{22}$, $R^{23}$, and $R^{24}$ of the 2-[(phosphinyl)aminyl] cyclic imine transition metal compound complexes having Structure APCITMC 2, Structure APCITMC 4, Structure APCITMC 6, and/or Structure APCITMC 8 independently can be hydrogen or an organyl group; alternatively, hydrogen or an organyl group consisting essentially of inert functional groups; alternatively, hydrogen or a hydrocarbyl group; alternatively an organyl group; alternatively, an organyl group consisting essentially of inert functional groups; alternatively, a hydrocarbyl group; or alternatively, hydrogen. In an embodiment, each organyl group which can be utilized for $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{15}$, a $C_1$ to $C_{10}$, or a $C_1$ to $C_5$ organyl group. In an embodiment, each organyl group consisting essentially of inert functional groups which can be utilized for $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, each hydrocarbyl group which can be utilized for $R^{12}$, $R^{13}$, $R^{14}$, $R^{21}$, $R^{22}$, $R^{23}$, and $R^{24}$ independently can be a $C_1$ to $C_{20}$, a $C_1$ to $C_{15}$, a $C_1$ to $C_{10}$, or a $C_1$ to $C_5$ hydrocarbyl group.

In an embodiment, $R^{12}$, $R^{13}$, and $R^{14}$ of the 2-[(phosphinyl)aminyl] cyclic imine transition metal compound complexes having Structure APCITMC 1, Structure APCITMC 3, Structure APCITMC 5, and/or Structure APCITMC 7, $R^{21}$ the 2-[(phosphinyl)aminyl] cyclic imine transition metal compound complexes having Structure APCITMC 2, Structure APCITMC 4, Structure APCITMC 6, Structure APCITMC 8, Structure APCITMC 10, Structure APCITMC 12, and/or Structure APCITMC 14, and $R^{22}$, $R^{23}$, and $R^{24}$ of the 2-[(phosphinyl)aminyl] cyclic imine transition metal compound complexes having Structure APCITMC 2, Structure APCITMC 4, Structure APCITMC 6, and/or Structure APCITMC 8 independently can be hydrogen, an alkyl group, or a substituted alkyl group; alternatively, hydrogen or an alkyl group; alternatively, hydrogen or a substituted alkyl group; alternatively, an alkyl group; alternatively, a substituted alkyl group; or alternatively, hydrogen. In any aspect or embodiment disclosed herein, each alkyl group which can be utilized as $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{10}$, or a $C_1$ to $C_5$ substituted alkyl group. In an embodiment, an alkyl group which can be utilized as $R^{12}$, $R^{13}$, $R^{14}$, $R^{21}$, $R^{22}$, $R^{23}$, and/or $R^{24}$ independently can be a methyl group, an ethyl group, a propyl group, a butyl group, a pentyl group, a hexyl group, a heptyl group, or an octyl group; alternatively a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the specific alkyl groups which can be utilized as $R^{12}$, $R^{13}$, $R^{14}$, $R^{21}$, $R^{22}$, $R^{23}$, and/or $R^{24}$ independently can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^{12}$, $R^{13}$, $R^{14}$, $R^{21}$, $R^{22}$, $R^{23}$, and/or $R^{24}$.

Generally, L of the 2-[(phosphinyl)aminyl] cyclic imine transition metal compound complexes having Structure APCITMC 1 and/or Structure APCITMC 2 can be —(CR'R")$_m$—. R', R", and n are independent elements of —$(CR'R'')_m$—. The independent descriptions of R', R", and m can be utilized without limitation, and in any combination, to further describe the L group having the formula —$(CR' R'')_m$— of the 2-[(phosphinyl)aminyl] cyclic imine transition metal compound complexes having Structure APCITMC 1 and/or Structure APCITMC 2.

In an embodiment, each R' and R" of —$(CR'R'')_m$— independently can be hydrogen or an organyl group; alternatively, hydrogen or an organyl group consisting essentially of inert functional groups; alternatively, hydrogen or a hydrocarbyl group; alternatively an organyl group; alternatively, an organyl group consisting essentially of inert functional groups; alternatively, a hydrocarbyl group; or alternatively, hydrogen. In an embodiment, each organyl group which can be utilized for R' and/or R" independently can be a $C_1$ to $C_{20}$, a $C_1$ to $C_{15}$, a $C_1$ to $C_{10}$, or a $C_1$ to $C_5$ organyl group. In an embodiment, each organyl group consisting essentially of inert functional groups which can be utilized for R' and/or R" independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, each hydrocarbyl group which can be utilized for R' and/or R" independently can be a $C_1$ to $C_{20}$, a $C_1$ to $C_{15}$, a $C_1$ to $C_{10}$ or, a $C_1$ to $C_5$ hydrocarbyl group.

In an embodiment, each R' and R" of —$(CR'R'')_m$— independently can be hydrogen, an alkyl group, or a substituted alkyl group; alternatively, hydrogen or an alkyl group; alternatively, hydrogen or a substituted alkyl group; alternatively, an alkyl group; alternatively, a substituted alkyl group; or alternatively, hydrogen. In any aspect or embodiment disclosed herein, each alkyl group which can be utilized as R' and/or R" independently can be a $C_1$ to $C_{20}$, a $C_1$ to $C_{10}$, or $C_1$ to $C_5$ alkyl group. In any aspect or embodiment disclosed herein, each substituted alkyl group which can be utilized as R' and/or R" independently can be a $C_1$ to $C_{20}$, a $C_1$ to $C_{10}$, or a $C_1$ to $C_5$ substituted alkyl group. In an embodiment, each alkyl group which can be utilized as R' and/or R" independently can be a methyl group, an ethyl group, or a propyl group; alternatively, a methyl group; alternatively, an ethyl group; alternatively, a propyl group. In some embodiments, the specific alkyl groups which can be utilized as R' and/or R" independently can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as R' and/or R".

In an embodiment, m of —$(CR'R'')_m$— can be 1, 2, or 3. In other embodiments, m of —$(CR'R'')_m$— can be 1; alternatively, 2; or alternatively, 3.

In some embodiments, L of the 2-[(phosphinyl)aminyl] cyclic imine transition metal compound complexes having Structure APCITMC 1 and/or Structure APCITMC 2 can be —(C(R')(R''))—, —(C(R')(R'')C(R')(R''))—, or —(C(R')(R'')C(R')(R'')C(R')(R''))—; alternatively, —(C(R')(R''))—; alternatively, —(C(R')(R'')C(R')(R''))—; or alternatively, or —(C(R')(R'')C(R')(R'')C(R')(R''))—. In some particular embodiments, L of the 2-[(phosphinyl)aminyl] cyclic imine transition metal compound complexes having Structure APCITMC 1 and/or Structure APCITMC 2 can be a methylene group (—$CH_2$), an eth-1,2-ylene group (—$CH_2CH_2$—), or a prop-1,3-ylene group (—$CH_2CH_2CH_2$—); alternatively, a methylene group (—$CH_2$); alternatively, an eth-1,2-ylene group (—$CH_2CH_2$—); or alternatively, a prop-1,3-ylene group (—$CH_2CH_2CH_2$—).

In a particular embodiment of the 2-[(phosphinyl)aminyl] cyclic imine transition metal compound complexes having Structure APCITMC 1, Structure APCITMC 3, Structure APCITMC 5, and/or Structure APCITMC 7 which can be utilized in the catalyst systems and the processes described herein, $R^{11}$ and $R^{13}$ or $R^{14}$ can be joined to form a ring or a ring system. In another particular embodiment of the 2-[(phosphinyl)aminyl] cyclic imine transition metal compound complexes having Structure APCITMC 1, Structure APCITMC 3, Structure APCITMC 5, and/or Structure APCITMC 7, L can be —(C(R')(R''))—, —(C(R')(R'')C(R')(R''))—, or —(C(R')(R'')C(R')(R'')C(R')(R''))— and $R^{11}$ and $R^{13}$ or $R^{14}$, can be joined to form a ring or a ring system. In yet another particular embodiment of the 2-[(phosphinyl)aminyl] cyclic imine transition metal compound complexes having Structure APCITMC 1, Structure APCITMC 3, Structure APCITMC 5, and/or Structure APCITMC 7, L can be a methylene group (—$CH_2$), an eth-1,2-ylene group (—$CH_2CH_2$—), or a prop-1,3-ylene group (—$CH_2CH_2CH_2$—) and $R^{11}$ and $R^{13}$ or $R^{14}$, can be joined to form a ring or a ring system. In some embodiments, the joining of $R^{11}$ and $R^{13}$ or $R^{14}$ can form a cyclopentyl ring or a cyclohexyl ring; alternatively, a cyclopentyl ring; or alternatively, a cyclohexyl ring. Depending on the identities of the $R^{11}$ and $R^{13}$ or $R^{14}$ groups the cyclopentyl ring and/or the cyclohexyl ring form by the joining of $R^{11}$ and $R^{13}$ or $R^{14}$ can be substituted or unsubstituted; alternatively, substituted; or alternatively, unsubstituted. Substituent groups general and specific are independently disclosed herein and these groups can be utilized without limitation to further describe a substituted ring or ring system formed by the joining of $R^{11}$ and $R^{13}$ or $R^{14}$.

In a particular embodiment of the 2-[(phosphinyl)aminyl] cyclic imine transition metal compound complexes having Structure APCITMC 1, Structure APCITMC 3, Structure APCITMC 5, and/or Structure APCITMC 7 which can be utilized in the catalyst systems and the processes described herein, $R^{11}$ can be any non-hydrogen substituted group described herein for $R^{11}$, and $R^{12}$, $R^{13}$, and $R^{14}$ can be hydrogen. In another particular embodiment of the 2-[(phosphinyl)aminyl] cyclic imine transition metal compound complexes having Structure APCITMC 2, Structure APCITMC 4, Structure APCITMC 6, and/or Structure APCITMC 8 which can be utilized in the catalyst systems and the processes described herein, $R^{21}$ can be any non-hydrogen substituted group described herein for $R^{21}$, and $R^{22}$, $R^{23}$, and $R^{24}$ can be hydrogen.

In a particular embodiment of the 2-[(phosphinyl)aminyl] cyclic imine transition metal compound complexes having Structure APCITMC 1, Structure APCITMC 3, Structure APCITMC 5, and/or Structure APCITMC 7 which can be utilized in the catalyst systems and the processes described herein, L can be —(C(R')(R''))—, —(C(R')(R'')C(R')(R''))—, or —(C(R')(R'')C(R')(R'')C(R')(R''))—, $R^{11}$ can be any non-hydrogen substituted group described herein for $R^{11}$, and $R^{12}$, $R^{13}$, and $R^{14}$ can be hydrogen. In another particular embodiment of the 2-[(phosphinyl)aminyl] cyclic imine transition metal compound complexes having Structure APCITMC 1, Structure APCITMC 3, Structure APCITMC 5, and/or Structure APCITMC 7 which can be utilized in the catalyst systems and the processes described herein, L can be a methylene group (—$CH_2$), an eth-1,2-ylene group (—$CH_2CH_2$—), or a prop-1,3-ylene group (—$CH_2CH_2CH_2$—), $R^{11}$ can be any non-hydrogen substituted group described herein for $R^{11}$, and $R^{12}$, $R^{13}$, and $R^{14}$ can be hydrogen. In yet another particular embodiment of the 2-[(phosphinyl)aminyl] cyclic imine transition metal compound complexes having Structure APCITMC 2, Structure APCITMC 4, Structure APCITMC 6, and/or Structure APCITMC 8 which can be utilized in the catalyst systems and the processes described herein, $R^{21}$ can be any non-hydrogen substituted group described herein for $R^{21}$, and $R^{22}$, $R^{23}$, and $R^{24}$ can be hydrogen. In a further particular embodiments, of the 2-[(phosphinyl)aminyl] cyclic imine transition metal compound complexes having Structure APCITMC 2, Structure APCITMC 4, Structure APCITMC 6, and/or Structure APCITMC 8 which can be utilized in the catalyst systems and the processes described herein, L can be a methylene group (—$CH_2$), an eth-1,2-ylene group (—$CH_2CH_2$—), or a prop-1,3-ylene group (—$CH_2CH_2CH_2$—), $R^{21}$ can be any non-hydrogen substituted group described herein for $R^{21}$, and $R^{22}$, $R^{23}$, and $R^{24}$ can be hydrogen.

The transition metal compound of the 2-[(phosphinyl)aminyl] cyclic imine transition metal compound complexes described herein can have the formula $MX_p$ where, M represent the transition metal, X represents a monoanionic ligand, and p represents the number of monoanionic ligands (and the oxidation state of the transition metal in the transition metal compound). The transition metal (M), the monoanionic ligand (X), and p are independent elements of the transition metal compound that are independently described herein. The independent descriptions of the transition metal, the monoanionic ligand (X), and p can be utilized without limitation, and in any combination, to further describe the transition metal compound ($MX_p$) of the 2-[(phosphinyl)aminyl] cyclic imine transition metal compound complexes.

Generally, the transition metal atom of the transition metal compound, $MX_p$, can be any transition metal atom. In an embodiment, the transition metal atom of the transition metal compound can comprise, or consist essentially of, a Group 3-12, a Group 4-10, a Group 6-9, or a Group 7-8 transition metal. In some embodiments, the transition metal atom of the transition metal compound can comprise, or consist essentially of, a Group 4 transition metal; alternatively, a Group 5 transition metal; alternatively, a Group 6 transition metal; alternatively, a Group 7 transition metal; alternatively, a Group 8 transition metal; alternatively, a Group 9 transition metal; or alternatively, a Group 10 transition metal. In an embodiment, the transition metal atom of the transition metal compound can comprise, or consist essentially of, titanium, zirconium, hafnium, vanadium, niobium, tantalum, chromium, molybdenum, tungsten, manganese, iron, cobalt, nickel, palladium, platinum, copper, or zinc; alternatively, titanium, zirconium, vanadium, chromium, molybdenum, tungsten, iron, cobalt, nickel, palladium, or platinum; alternatively, chromium, iron, cobalt, or nickel; alternatively, titanium, zirconium, or hafnium; alternatively, vanadium or niobium; alternatively, chromium, molybdenum, or tungsten; alternatively, iron or cobalt; or alternatively, nickel, palladium, platinum, copper, or zinc. In other embodiments, the metal salt can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc.

Generally, the transition metal atom of the transition metal compound, $MX_p$, can have any positive oxidation state available to the transition metal atom. In an embodiment, the transition metal atom can have an oxidation state of from +2 to +6; alternatively, from +2 to +4; or alternatively, from +2 to +3. In some embodiments, the transition metal atom of the transition metal compound, $MX_p$, can have an oxidation state of +1; alternatively, +2; alternatively, +3; or alternatively, +4.

The monoanion, X, of the transition metal compound can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion, X, of the transition metal compound independently can be fluorine, chlorine, bromine, or iodine; or alternatively, chlorine, bromine, or iodine. In an embodiment, each halide monoanion, X, of the transition metal compound can be chlorine; alternatively, bromine; or alternatively, iodine.

Generally, each carboxylate monoanion of the transition metal compound independently can be a $C_1$ to $C_{20}$ carboxylate; or alternatively, a $C_1$ to $C_{10}$ carboxylate. In an embodiment, each carboxylate monoanion of the transition metal compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanion of the transition metal compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), n-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanion of the transition metal compound can be triflate (trifluoroacetate).

Generally, each β-diketonate monoanion of the transition metal compound independently can be any $C_1$ to $C_{20}$ a β-diketonate; or alternatively, any $C_1$ to $C_{10}$ β-diketonate. In an embodiment, each β-diketonate monoanion of the transition metal compound independently can be acetylacetonate (i.e., 2,4-pentanedionate), hexafluoroacetylacetone (i.e., 1,1,1,5,5,5-hexafluoro-2,4-pentanedionate), or benzoylacetonate); alternatively, acetylacetonate; alternatively, hexafluoroacetylacetone; or alternatively, benzoylacetonate.

Generally, each hydrocarboxide monoanion of the transition metal compound independently can be any $C_1$ to $C_{20}$ hydrocarboxide; or alternatively, any $C_1$ to $C_{10}$ hydrocarboxide. In an embodiment, each hydrocarboxide monoanion of the transition metal compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion of the transition metal compound independently can be methoxide, ethoxide, a propoxide, or a butoxide. In some embodiments, each alkoxide monoanion of the transition metal compound independently can be methoxide, ethoxide, isopropoxide, or tert-butoxide; alternatively, methoxide; alternatively, an ethoxide; alternatively, an isopropoxide; or alternatively, a tert-butoxide. In an aspect, the aryloxide can be phenoxide.

In a particular aspect, the transition metal compound of the 2-[(phosphinyl)aminyl] cyclic imine transition metal compound complexes can be chromium compound having the formula $CrX_p$. In such instances $CrX_p$ can replace $MX_p$ in any 2-[(phosphinyl)aminyl] cyclic imine transition metal compound complex presented herein and the 2-[(phosphinyl)aminyl] cyclic imine transition metal compound complexes can be referred to a 2-[(phosphinyl)aminyl] cyclic imine chromium compound complex. Generally, the chromium compound of the 2-[(phosphinyl)aminyl] cyclic imine transition metal compound complexes described herein has the formula $CrX_p$ where X represents a monoanionic ligand, and p represent the number of monoanionic ligands (and the oxidation state of the chromium in the chromium compound). The monoanionic ligand (X) and p are independent elements of the chromium compound and are independently described herein. The independent descriptions of the monoanionic ligand (X) and p can be utilized without limitation, and in any combination, to further describe the chromium compound of the 2-[(phosphinyl)aminyl] cyclic imine transition metal compound complexes.

In a non-limiting embodiment, the chromium compound of any of the 2-[(phosphinyl)aminyl] cyclic imine transition metal compound complexes described herein can comprise, can consist essentially of, or consist of, a chromium(II) halide, a chromium(III) halide, a chromium(II) carboxylate, a chromium(III) carboxylate, a chromium(II) β-diketonate, or a chromium(III) β-diketonate. In some non-limiting embodiments, the chromium compound of any of the 2-[(phosphinyl)aminyl] cyclic imine transition metal compound complexes described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any of the 2-[(phosphinyl)aminyl] cyclic imine transition metal compound complexes described herein can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any of the 2-[(phosphinyl)aminyl] cyclic imine transition metal compound complexes described herein can comprise, can consist essentially of, or consist of, chromium(II) chloride, chromium(III) chloride, chromium(II) fluoride, chromium(III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (II) benzoylacetonate, or chromium(III) benzoylacetonate. In some non-limiting embodiments, the chromium compound of any of the 2-[(phosphinyl)aminyl] cyclic imine transition metal compound complexes described herein can comprise, can consist essentially of, or consist of, chromium (III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate. In further embodiments, the chromium compound of any of the 2-[(phosphinyl)aminyl] cyclic imine transition metal compound complexes described herein can be chromium(III) chloride, or chromium(III) acetylacetonate; alternatively, chromium(III) chloride; or alternatively, chromium(III) acetylacetonate.

While not shown, it should be appreciated that a neutral ligand can be associated with the 2-[(phosphinyl)aminyl] cyclic imine transition metal compound complexes described herein. Additionally it should be understood that while the 2-[(phosphinyl)aminyl] cyclic imine transition metal compound complexes provided herein do not formally show the presence of a neutral ligand, the 2-[(phosphinyl) aminyl] cyclic imine transition metal compound complexes having neutral ligands (e.g., nitriles and ethers, among others) are fully contemplated as potential 2-[(phosphinyl) aminyl] cyclic imine transition metal compound complexes that can be used in the catalyst system and process aspects and embodiments of the herein described inventions.

Generally, the organoaluminum compound utilized in the catalyst systems disclosed herein can be any organoaluminum compound which can catalyze the formation of an oligomer product. In an aspect, the organoaluminum compound can be an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum halide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide. In some embodiments, the alkylaluminum compound can be an aluminoxane.

In an aspect, each alkyl group of any alkylaluminum compound disclosed herein (trialkylaluminum, alkylaluminum halide, or alkylaluminum alkoxide) independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of any alkylaluminum compound disclosed herein independently can be, comprise, or consist essentially of, a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each halide of any alkylaluminum halide disclosed herein can be, comprise, or consist essentially of, chloride, bromide, or iodide. In some embodiments, each halide of any alkylaluminum halide disclosed herein can be, comprise, or consist essentially of, chloride or bromide; or alternatively, chloride.

In an aspect, each alkoxide group of any alkylaluminum alkoxide disclosed herein independently can be, comprise, or consist essentially of, a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any alkylaluminum alkoxide disclosed herein independently can be, comprise, or consist essentially of, a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be, comprise, or consist essentially of, a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can be, comprise, or consist essentially of, diethylaluminum chloride, diethylaluminum bromide, ethylaluminum dichloride, ethylaluminum sesquichloride, or mixtures thereof. In some non-limiting embodiments, the alkylaluminum halide can be, comprise, or consist essentially of, diethylaluminum chloride, ethylaluminum dichloride, ethylaluminum sesquichloride, or mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride.

In particular aspects of this invention, the organoaluminum compound can comprise trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, or combinations thereof.

In a non-limiting embodiment, the aluminoxane can have a repeating unit characterized by the Formula I:

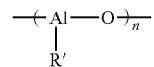

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each alkyl group of the aluminoxane independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of the aluminoxane independently can be, comprise, or consist essentially of, a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group or the aluminoxane independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butylaluminoxane, 1-pentyl-aluminoxane, 2-pentylaluminoxane, 3-pentyl-aluminoxane, iso-pentylaluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutylaluminoxane, t-butylaluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

In an embodiment, the catalyst systems can have a minimum aluminum of the organoaluminum compound (e.g., aluminoxane, among others) to transition metal of the 2-[(phosphinyl)aminyl] cyclic imine transition metal compound complex molar ratio (i.e., minimum Al to M molar ratio) of 10:1, 50:1, 75:1, or 100:1. In other embodiments, the catalyst systems can have a maximum aluminum of the organoaluminum compound (e.g., aluminoxane, among others) to transition metal of the 2-[(phosphinyl)aminyl] cyclic imine transition metal compound complex molar ratio molar ratio (i.e., maximum Al to M molar ratio) of 5,000:1, 3,000:1, 2,000:1, 1,500:1, or 1,000:1. In an embodiment, the catalyst systems can have an Al to M molar ratio ranging from any minimum Al to M molar ratio disclosed herein to any maximum Al to M molar ratio disclosed herein. In a non-limiting embodiment, the Al to M molar ratio can range from 10:1 to 5,000:1, from 50:1 to 3,000:1, from 50:1 to 3,000:1, from 75:1 to 2,000:1, from 100:1 to 2,000:1, of from 100:1 to 1,000:1. Other Al to M molar ratio ranges that can be utilized are readily apparent to those skilled in the art with the aid of this disclosure. It should be noted that when a specific transition metal is used for the 2-[(phosphinyl)aminyl] cyclic imine transition metal compound complex (e.g., chromium, Cr), the specific metal can be utilized in place of the general transition metal in the minimum, maximum, and ranges for the Al to M molar ratios (e.g., Al to Cr molar ratios).

Generally, the catalyst systems can be prepared by contacting the 2-[(phosphinyl)aminyl] cyclic imine transition metal compound complex (any described herein) and the organoaluminum compound (any described herein) to form a catalyst system. In an embodiment, the catalyst systems can be prepared by 1) contacting the 2-[(phosphinyl)aminyl] cyclic imine transition metal compound complex (any described herein) and the organoaluminum compound (any described herein) to form a catalyst system mixture, and 2) aging the catalyst system mixture in the substantial absence of ethylene to form an aged catalyst system mixture. In a non-limiting embodiment, a substantial absence of ethylene can be a maximum molar ratio of ethylene to 2-[(phosphinyl)aminyl] cyclic imine transition metal compound complex of 5:1, 4:1, 3:1, 2:1, 1:1, 0.5:1, 0.25:1, or 0.1:1. In some non-limiting embodiments, the substantial absence of ethylene can be a maximum ethylene partial pressure 10 psig (69 kPa), 5 psig (34 kPa), 4 psig (28 kPa), 3 psig (21 kPa), 2 psig (14 kPa), 1 psig (7 kPa), or 0.5 psig (3.5 kPa). In some embodiments, the catalyst systems can be formed by contacting a diluent and/or a solvent with the 2-[(phosphinyl)aminyl] cyclic imine transition metal compound complex (any described herein) and the organoaluminum compound (any described herein). In an embodiment, the diluent and/or solvent can be any organic reaction medium described herein. In an embodiment, the diluent and/or solvent can be the same as the organic reaction medium; alternatively the diluent and/or solvent differs from the organic reaction medium.

In an embodiment the catalyst system mixture can be aged for a period of time. Typically, the minimum aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the aging time can include from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the aging time are readily apparent from this disclosure.

In further embodiments, the catalyst system mixture can be aged at any suitable temperature, ranging from sub-ambient temperatures, to ambient temperature (approximately 25° C.), to elevated temperatures. While not limited thereto, the catalyst system mixture can be aged at a temperature in a range from 0° C. to 100° C., from 10° C. to 75° C., from 15° C. to 60° C., or from 20° C. to 40° C. In these and other embodiments, these temperature ranges also are meant to encompass circumstances where the catalyst system mixture can be aged at a series of different temperatures, instead of at a single fixed temperature, falling within the respective ranges.

In an aspect, the inventions disclosed herein can include a process comprising contacting i) ethylene, ii) a catalyst system comprising (a) a 2-[(phosphinyl)aminyl] cyclic imine transition metal compound complex, and (b) an organoaluminum compound, and iii) optionally hydrogen to form an oligomer product. In an embodiment, the oligomer product can be formed in a reaction zone. In a combinable embodiment, the process can further comprise contacting ethylene, the catalyst system, and the optional hydrogen in an organic reaction medium to form the oligomer product. In an embodiment, the oligomer product can be formed under conditions capable of forming an oligomer product. In any embodiment or aspect in which the oligomer product is formed in a reaction zone, the process can further comprise removing a reaction zone effluent comprising the oligomer product from the reaction zone and optionally isolating one or more oligomer products from the reaction zone effluent. In some embodiments, the process can further comprise forming the catalyst system using any catalyst system formation process described herein.

In an embodiment, the reaction zone utilized in the processes described herein can comprise any reactor which can oligomerize ethylene to an oligomer product. In an embodiment, the reaction zone can comprise a stirred tank reactor, a plug flow reactor, or any combination thereof; alternatively, a stirred tank reactor; or alternatively, a plug flow reactor. In an embodiment, the reaction zone of any process, system, or reaction system described herein can comprise an autoclave reactor, continuous stirred tank reactor, a loop reactor, a gas phase reactor, a solution reactor, a tubular reactor, a recycle reactor, a bubble reactor, or any combination thereof; alternatively, autoclave reactor; alternatively, stirred tank reactor; alternatively, a loop reactor; alternatively, a gas phase reactor; alternatively, a solution reactor; alternatively, a tubular reactor; alternatively, a recycle reactor; or alternatively, a bubble reactor. In some embodiments, the reaction zone can comprise multiple reactors; or alternatively, only on reactor. When multiple reactors are present, each of the reactors can be the same or different types of reactors.

In an embodiment, the process described herein can be a batch process or a continuous process; alternatively, a batch process; or alternatively, a continuous process. In a continuous process embodiment, the process can further comprise periodically or continuously introducing/feeding ethylene, a catalyst system, optionally organic reaction medium, and/or optionally hydrogen to the reaction zone and/or periodically or continuously removing a reaction zone effluent from the reaction zone.

In an embodiment the 2-[(phosphinyl)aminyl] cyclic imine transition metal compound complexes can be utilized in a catalyst system in an ethylene oligomerization process. In an embodiment, conditions under which the oligomer product can be form can include one or more of catalyst system component ratios, transition metal (e.g., chromium) concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity. Catalyst system component ratios, transition metal (e.g., chromium) concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity are independently described herein and these independent descriptions can be used without limitation and in any combination to describe the conditions at which the oligomer product can be formed (or alternatively, to describe the reaction zone conditions).

In an embodiment, the oligomer product can be formed (or the reaction zone can operate) at a minimum reaction zone transition metal concentration of the 2-[(phosphinyl)aminyl] cyclic imine transition metal compound complex (i e, minimum transition metal, M, concentration) of $1 \times 10^{-6}$ equivalents/liter, $1 \times 10^{-5}$ equivalents/liter, or $5 \times 10^4$ equivalents/liter; additionally or alternatively, at a maximum reaction zone transition metal concentration of the 2-[(phosphinyl)aminyl] cyclic imine transition metal compound complex (i.e., maximum transition metal, M, concentration) of 1 equivalents/liter, $5 \times 10^{-1}$ equivalents/liter, or $1 \times 10^{-1}$ equivalents/liter. In an embodiment, the oligomer product can be formed (or the reaction zone can operate) at a reaction zone transition metal concentration ranging from any minimum transition metal concentration disclosed herein to any maximum transition metal concentration disclosed herein. In a non-limiting embodiment, the reaction zone transition metal concentration can range from $1 \times 10^{-6}$ equivalents/liter to 1 equivalents/liter, from $1 \times 10^{-5}$ equivalents/liter to $5 \times 10^{-1}$ equivalents/liter, from $5 \times 10^4$ equivalents/liter to $1 \times 10^{-1}$ equivalents/liter. Other transition metal concentration ranges that can be utilized are readily apparent to those skilled in the art with the aid of this disclosure In a non-limiting embodiment where the transition metal comprises chromium, the oligomer product can be formed (or the reaction zone can operate) at a minimum reaction zone chromium concentration of the 2-[(phosphinyl)aminyl] cyclic imine chromium compound complex (i e, minimum chromium concentration) of $1 \times 10^{-6}$ equivalents/liter, $1 \times 10^{-5}$ equivalents/liter, or $5 \times 10^{-4}$ equivalents/liter; additionally or alternatively, at a maximum reaction zone chromium concentration of the 2-[(phosphinyl)aminyl] cyclic imine chromium compound complex (i.e., maximum chromium concentration) of 1 equivalents/liter, $5 \times 10^{-1}$ equivalents/liter, or $1 \times 10^{-1}$ equivalents/liter. In an embodiment, the oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1 \times 10^{-6}$ equivalents/liter to 1 equivalents/liter, from $1 \times 10^{-5}$ equivalents/liter to $5 \times 10^{-1}$ equivalents/liter, from $5 \times 10^{-4}$ equivalents/liter to $1 \times 10^{-1}$ equivalents/liter. Other reaction zone chromium concentration ranges that can be utilized are readily apparent to those skilled in the art with the aid of this disclosure.

In an embodiment, the oligomer product can be formed (or the reaction zone can operate) at a minimum pressure of 5 psi (34.5 kPa), 50 psi (345 kPa); 100 psi (689 kPa), 150 psi (1.03 MPa), 250 psi (1.72 MPa), 500 psi (3.5 MPa), or 600 psi (4.1 MPa); additionally or alternatively, at a maximum pressure of 2,500 psi (17.2 MPa), 2,000 psi (13.8 MPa), 1,500 psi (10.3 MPa), 1250 psi (8.62 MPa), 1400 psi (9.65 MPa), 1250 psi (8.62 MPa), or 1000 psi (6.89 MPa). In an embodiment, the oligomer product can be formed (or the reaction zone can operate) at a pressure ranging from any minimum pressure disclosed herein to any maximum pressure disclosed herein. In some non-limiting embodiments, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 250 psi (1.72 MPa) to 1000 psig (6.89 MPa), or from 600 psi (4.1 MPa) to 1400 psi (9.65 MPa). Other pressure ranges that can be utilized are readily apparent to those skilled in the art with the aid of this disclosure.

In an embodiment, the oligomer product can be formed (or the reaction zone can operate) at a minimum ethylene partial pressure of 5 psi (34.5 kPa), 50 psi (345 kPa); 100 psi (689 kPa), 150 psi (1.03 MPa), 250 psi (1.72 MPa), or 500 psi (3.5 MPa); additionally or alternatively, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at an ethylene partial pressure ranging from any minimum ethylene partial pressure disclosed herein to any maximum ethylene partial pressure disclosed herein. In some non-limiting embodiments, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 150 psi (1.03 MPa) to 1250 psi (8.62 MPa), or from 250 psi (1.72 MPa) to 1000 psi (6.89 MPa). Other ethylene partial pressure ranges are readily apparent to those skilled in the art with the aid of this disclosure.

In an embodiment, the oligomer product can be formed (or the reaction zone can operate) at a minimum ethylene concentration of 4 mass %, 10 mass %, 25 mass %, 35 mass %, or 40 mass % based upon the total mass in the reaction zone; additionally or alternatively, at a maximum ethylene concentration of 70 mass %, 65 mass %, 60 mass %, 55 mass %, 50 mass %, 48 mass % based upon the total mass in the reaction zone. In an embodiment, the oligomer product can be formed (or the reaction zone can operate) at an ethylene concentration ranging from any minimum ethylene concentration disclosed herein to any maximum ethylene concentration disclosed herein. In some non-limiting embodiments, the oligomer product can be formed (or the reaction zone can operate) at an ethylene concentration from 4 mass % to 60 mass %, from 4 mass % to 60 mass %, from 10 mass % to 60 mass %, from 25 mass % to 55 mass %, from 35 mass % to 50 mass %, or from 40 mass % to 48 mass % based upon the total mass in the reaction zone. Other ethylene concentration ranges that can be utilized are readily apparent to those skilled in the art with the aid of this disclosure.

In an embodiment, the oligomer product can be formed (or the reaction zone can operate) at a minimum ethylene:

transition metal molar ratio 100,000:1, 280,000:1, 460,000:1, or 750,000:1; additionally or alternatively, at a maximum ethylene:chromium mass ratio of 9,500,000:1, 4,600,000:1, 2,800,000:1, or 1,900,000:1. In an embodiment, the oligomer product can be formed (or the reaction zone can operate) at an ethylene:transition metal molar ratio ranging from any minimum ethylene:transition metal molar ratio disclosed herein to any maximum ethylene:chromium mass ratio disclosed herein. In some non-limiting embodiments, the oligomer product can be formed (or the reaction zone can operate) at an ethylene:transition metal molar ratio from 100,000:1 to 9,500,000:1, 280,000:1 to 4,600,000:1, 460,000:1 to 2,800,000:1, or 750,000:1 to 1,900,000:1. Other ethylene:transition metal molar ratio ranges that can be utilized are readily apparent to those skilled in the art with the aid of this disclosure.

In a non-limiting embodiment where the transition metal of the 2-[(phosphinyl)aminyl] cyclic imine transition metal compound complex is chromium, the oligomer product can be formed (or the reaction zone can operate) at a minimum ethylene:chromium mass ratio of 50,000:1, 150,000:1, 250,000:1, or 400,000:1; additionally or alternatively, at a maximum ethylene:chromium mass ratio of 5,000,000:1, 2,500,000:1, 1,500,000:1, or 1,000,000:1. In an embodiment, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the oligomer product can be formed (or the reaction zone can operate) at an ethylene:chromium mass ratio from 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure.

In an embodiment wherein hydrogen is utilized, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally, at a maximum hydrogen partial pressure of 200 psi (1.4 MPa)), 150 psi (1.03 MPa), 100 psi (689 kPa), 75 psig (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

In an embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); additionally or alternatively, at a maximum hydrogen to ethylene mass ratio of (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure In an embodiment, the oligomer product can be formed (or the reaction zone can operate) at a minimum hydrogen:transition metal molar ratio of 26:1, 1,300:1, 2,600:1, or 5,200:1; additionally or alternatively, at a maximum hydrogen:transition metal molar ratio of 2,600,000:1, 1,300,000:1, 260,000:1, or 78,000:1. In an embodiment, the oligomer product can be formed (or the reaction zone can operate) at a hydrogen:transition metal molar ratio ranging from any minimum hydrogen:transition metal molar ratio disclosed herein to any maximum hydrogen:transition metal molar ratio disclosed herein. In some non-limiting embodiments, the oligomer product can be formed (or the reaction zone can operate) at a hydrogen:transition metal molar ratio from 26:1 to 2,600,000:1, 1,300:1 to 1,300,000:1, 2,600:1 to 260,000:1, or 5,200:1 to 78,000:1. Other hydrogen:transition metal molar ratio ranges that can be utilized are readily apparent to those skilled in the art with the aid of this disclosure.

In a non-limiting embodiment where the transition metal of the 2-[(phosphinyl)aminyl] cyclic imine transition metal compound complex is chromium, the oligomer product can be formed (or the reaction zone can operate) at a minimum hydrogen:chromium mass ratio of 1:1, 50:1, 100:1, or 200:1; additionally or alternatively, at a maximum hydrogen:chromium mass ratio of 100,000:1, 50,000:1, 10,000:1, or 3,000:1. In an embodiment, the oligomer product can be formed (or the reaction zone can operate) at a hydrogen:chromium mass ratio ranging from any minimum hydrogen:chromium mass ratio disclosed herein to any maximum hydrogen:chromium mass ratio disclosed herein. In some non-limiting embodiments, the oligomer product can be formed (or the reaction zone can operate) at a hydrogen:chromium mass ratio from 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure.

In an embodiment, the oligomer product can be formed (or the reaction zone can operate) at a minimum temperature of 0° C., 25° C., 40° C., or 50° C. In some embodiments, the oligomer product can be formed (or the reaction zone can operate) at a maximum temperature of 200° C., 150° C., 100° C., or 90° C. In an embodiment, the oligomer product can be formed (or the reaction zone can operate) at a temperature ranging from any minimum temperature disclosed herein to any maximum temperature disclosed herein. In some non-limiting embodiments, the oligomer product can be formed (or the reaction zone can operate) at a temperature from 0° C. to 200° C., from 25° C. to 150° C., from 40° C. to 100° C., from 50° C. to 100° C., or from 50°

C. to 90° C. Other temperature ranges that can be utilized are readily apparent to those skilled in the art with the aid of this disclosure.

The reaction time (or residence time) can comprise any time that can produce the desired quantity of oligomer product; alternatively, any reaction time (or residence time) that can provide a desired catalyst system productivity; alternatively, any reaction time (or residence time) that can provide a desired ethylene conversion. Relating to forming the oligomer product, the oligomer product can be formed over a period of time (or an average time) that can produce the desired quantity of olefin product or polymer product, provide a desired catalyst system productivity, and/or provide a desired conversion of monomer. In some embodiments, the time can range from 1 minute to 5 hours; alternatively, ranges from 5 minutes to 2.5 hours; alternatively, ranges from 10 minutes to 2 hours; or alternatively, ranges from 15 minutes to 1.5 hours. In some embodiments (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

In an embodiment, the process described herein can have an ethylene conversion of at least 30%, 35%, 40%, or 45%. In another aspect the ethylene conversion can be a single pass conversion of at least 30%, 35%, 40%, or 45%.

In an embodiment, the processes described herein can have a catalyst system productivity of greater than 500,000 grams of oligomer per mole of transition metal, greater than 2,500,000 grams of oligomer per mole of transition metal, greater than 5,000,000 grams of oligomer per mole of transition metal, greater than 7,500,000 grams of oligomer per mole of transition metal, or greater than 10,000,000 grams of oligomer per mole of transition metal. In a non-limiting embodiment where the transition metal of the 2-[(phosphinyl)aminyl] cyclic imine transition metal compound complex is chromium, the processes described herein can have a catalyst system productivity of greater than 10,000 grams of oligomer per gram of chromium, greater than 50,000 grams of oligomer per gram of chromium, greater than 100,000 grams of oligomer per gram of chromium, greater than 150,000 grams of oligomer per gram of chromium, or greater than 200,000 grams of oligomer per gram of chromium.

Depending upon the catalyst system utilized, the processes described herein can be an ethylene oligomerization process, an ethylene trimerization process, an ethylene tetramerization process, or an ethylene trimerization and tetramerization process; alternatively, an ethylene oligomerization process; alternatively, an ethylene trimerization process; alternatively, an ethylene tetramerization process; or alternatively an ethylene trimerization and tetramerization process. In an ethylene trimerization embodiment, the oligomer product can comprise at least 70 wt. % hexenes, at least 75 wt. % hexenes, at least 80 wt. % hexenes, at least 85 wt. % hexenes, or at least 90 wt. % hexenes based upon the weight of the oligomer product. In some ethylene trimerization embodiments, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In an ethylene tetramerization embodiment, the oligomer product can comprise at least 70 wt. % octenes, at least 75 wt. % octenes, at least 80 wt. % octenes, at least 85 wt. % octenes, or at least 90 wt. % octenes based upon the weight of the oligomer product. In some ethylene tetramerization embodiments, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In an ethylene trimerization and tetramerization embodiment, the oligomer product can comprise at least 70 wt. % hexenes and octenes, at least 75 wt. % hexenes and octenes, at least 80 wt. % hexenes and octenes, at least 85 wt. % hexene and octenes, or at least 90 wt. % hexenes and octenes based upon the weight of the oligomer product. In some ethylene trimerization and tetramerization embodiments, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

In an aspect, the processes described herein can use an organic reaction medium. Generally, the organic reaction medium can act as a solvent and/or a diluent in the processes described herein. In an embodiment, the organic reaction medium can be a hydrocarbon, a halogenated hydrocarbon, or a combination thereof. Hydrocarbons and halogenated hydrocarbons which can be used as an organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as an organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as an organic reaction medium can be cyclic or acyclic and/or can be linear or branched, unless otherwise specified. Non-limiting examples of suitable acyclic aliphatic hydrocarbon organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as an organic reaction medium include cyclohexane, and methyl cyclohexane. Aromatic hydrocarbons which can be useful as an organic reaction medium include $C_6$ to $C_{10}$ aromatic hydrocarbons. Non-limiting examples of suitable aromatic hydrocarbons that can be utilized singly or in any combination as an organic reaction medium include benzene, toluene, xylene (including ortho-xylene, meta-xylene, para-xylene, or mixtures thereof), ethylbenzene, or combinations thereof. Halogenated aliphatic hydrocarbons which can be useful as an organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons. The halogenated aliphatic hydrocarbons which can be used as an organic reaction medium can be cyclic or acyclic and/or can be linear or branched, unless otherwise specified. Non-limiting examples of suitable halogenated aliphatic hydrocarbons which can be utilized as an organic reaction medium include methylene chloride, chloroform, carbon tetrachloride, dichloroethane, trichloroethane, and combinations thereof. Halogenated aromatic hydrocarbons which can be useful as an organic reaction medium include $C_6$ to $C_{20}$ halogenated aromatic hydrocarbons, or $C_6$ to $C_{10}$ halogenated aromatic hydrocarbons. Non-limiting examples of suitable halogenated aromatic hydrocarbons which can be used as a solvent include chlorobenzene, dichlorobenzene, or combinations thereof.

The choice of organic reaction medium can be made on the basis of convenience in processing. For example, isobutane can be chosen to be compatible with solvents and diluents used in processes using the product(s) of the process described herein (e.g., using the product for the formation of polymer in a subsequent processing step). In some embodiments, the organic reaction medium can be chosen to be easily separable from the one or more of the oligomer in the oligomer product. In some embodiments, an oligomer of the oligomer product can be utilized as the reaction system solvent. For example, when 1-hexene is an oligomer of an ethylene trimerization process, 1-hexene can be chosen as the reaction system solvent to decrease the need for separation.

Various aspects and embodiments described herein can refer to a substituted group or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy group can be a $C_1$ to $C_{10}$ hydrocarboxy group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

Having described the various compounds, complexes, and processes, aspects and embodiments of the compounds, complexes, and/or processes can include, but are not limited to:

A first embodiment which is a catalyst system comprising i) a 2-[(phosphinyl)aminyl] cyclic imine transition metal compound complex and ii) an organoaluminum compound.

A second embodiment which is the catalyst system of the first embodiment, wherein the 2-[(phosphinyl)aminyl] cyclic imine transition metal compound complex has the structure:

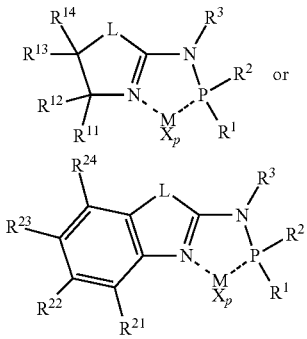

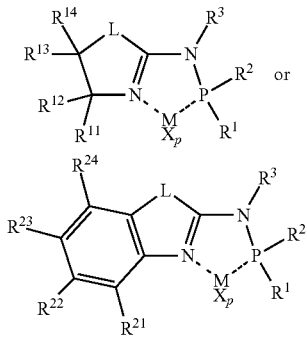

wherein $R^1$ and/or $R^2$ are each independently a $C_1$ to $C_{20}$ organyl group consisting essentially of inert functional groups, $R^3$ is hydrogen or a $C_1$ to $C_{20}$ organyl group, L is —$(CR'R'')_m$— where each R' and R" independently is a hydrogen or a $C_1$ to $C_{10}$ organyl group consisting essentially of inert functional groups and m is 1, 2, or 3, $R^{11}$ is hydrogen or a $C_1$ to $C_{20}$ organyl group consisting essentially of inert functional groups, $R^{12}$, $R^{13}$, $R^{14}$, $R^{21}$, $R^{22}$, $R^{23}$, and $R^{24}$ are each independently hydrogen or a $C_1$ to $C_{20}$ organyl group consisting essentially of inert functional groups, optionally $R^{11}$ and $R^{13}$ or $R^{14}$ are joined to form a ring or ring system, and $MX_p$ represents a transition metal compound where M is a transition metal, X is a monoanion, and p ranges from 2 to 6.

A third embodiment which is the catalyst system of any of the first and second embodiments, wherein L is —$(CH_2)_m$— where m is 1, 2, or 3, $R^{11}$ is a $C_1$ to $C_{10}$ alkyl group and $R^{12}$, $R^{13}$, and $R^{14}$ are hydrogen, $R^{21}$ is hydrogen or a $C_1$ to $C_{10}$ alkyl group, and $R^{22}$, $R^{23}$, and $R^{24}$ are hydrogen.

A fourth embodiment which is the catalyst system of any of the first through third embodiments wherein $R^3$ is hydrogen.

A fifth embodiment which is the catalyst system of any of the first through fourth embodiments, wherein the transition metal compound comprises a chromium(III) carboxylate, a chromium(III) β-diketonate, or a chromium(III) halide.

A sixth embodiment which is the catalyst system of any of the first through fifth embodiments, wherein the organoaluminum compound comprises an aluminoxane.

A seventh embodiment which is the catalyst system of the sixth embodiment, wherein the aluminoxane comprises methylaluminoxane, modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentyl-aluminoxane, iso-pentylaluminoxane, neopentylaluminoxane, or mixtures thereof.

An eighth embodiment which is the catalyst system of the sixth embodiment, wherein the aluminoxane comprises modified methylaluminoxane.

A ninth embodiment which is the catalyst system of the sixth through the eighth embodiments, wherein an aluminum of the aluminoxane to transition metal of the 2-[(phosphinyl)aminyl] cyclic imine transition metal compound complex molar ratio is in the range of from 10:1 to 5,000:1.

A tenth embodiment which is the catalyst system of any of the first through ninth embodiments, wherein the 2-[(phosphinyl)aminyl] cyclic imine transition metal compound complex has the structure:

wherein $R^1$ and/or $R^2$ are each independently a $C_1$ to $C_{20}$ organyl group consisting essentially of inert functional groups, $R^3$ is hydrogen, L is —$(CH_2)_m$— where m is 1, 2, or 3, $R^{11}$ is a $C_1$ to $C_{10}$ alkyl group and $R^{12}$, $R^{13}$, and $R^{14}$ are hydrogen, $R^{21}$ is hydrogen or a $C_1$ to $C_{10}$ alkyl group, and $R^{22}$, $R^{23}$, and $R^{24}$ are hydrogen, and $MX_p$ is chromium(III) chloride, the organoaluminum compound is an aluminoxane, and an aluminum of the aluminoxane to chromium of the 2-[(phosphinyl)aminyl] cyclic imine chromium compound complex molar ratio is in the range of from 10:1 to 5,000:1.

An eleventh embodiment which is a process comprising contacting i) an ethylene, ii) a catalyst system comprising (a) a 2-[(phosphinyl)aminyl] cyclic imine transition metal compound complex, and (b) an organoaluminum compound, and iii) optionally hydrogen to form an oligomer product.

A twelfth embodiment which is the process of the eleventh embodiment, wherein the 2-[(phosphinyl)aminyl] cyclic imine transition metal compound complex has the general structure:

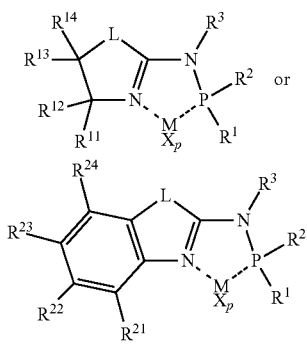

wherein $R^1$ and/or $R^2$ are each independently a $C_1$ to $C_{20}$ organyl group consisting essentially of inert functional groups, $R^3$ is hydrogen or an $C_1$ to $C_{20}$ organyl group, L is —$(CR'R'')_m$— where each R' and R" independently is a hydrogen or a $C_1$ to $C_{10}$ organyl group consisting essentially of inert functional groups and m is 1, 2, or 3, $R^{11}$ is hydrogen or a $C_1$ to $C_{20}$ organyl group consisting essentially of inert functional groups, $R^{12}$, $R^{13}$, $R^{14}$, $R^{21}$, $R^{22}$, $R^{23}$, and $R^{24}$, are each independently hydrogen or a $C_1$ to $C_{20}$ organyl group consisting essentially of inert functional groups, optionally $R^{11}$ and $R^{13}$ or $R^{14}$ are joined to form a ring or ring system, and $MX_p$ represents a transition metal compound where M is a transition metal, X is a monoanion, and p ranges from 2 to 6.

A thirteenth embodiment which is the process of any of the eleventh and twelfth embodiments, wherein the transition metal compound comprises a chromium(III) carboxylate, a chromium(III) β-diketonate, or a chromium(III) halide.

A fourteenth embodiment which is the process of any of the eleventh through thirteenth embodiments, wherein the organoaluminum compound comprises an aluminoxane.

A fifteenth embodiment which is the process of any of the eleventh through fourteenth embodiments, wherein the 2-[(phosphinyl)aminyl] cyclic imine transition metal compound complex has the general structure:

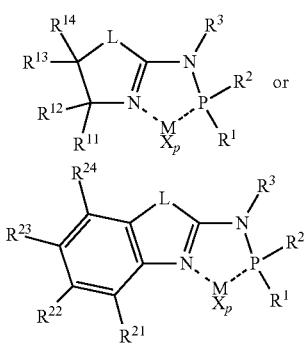

wherein $R^1$ and/or $R^2$ are each independently a $C_1$ to $C_{20}$ organyl group consisting essentially of inert functional groups, $R^3$ is hydrogen, L is —$(CH_2)_m$— where m is 1, 2, or 3, $R^{11}$ is a $C_1$ to $C_{10}$ alkyl group and $R^{12}$, $R^{13}$, and $R^{14}$ are hydrogen, $R^{21}$ is hydrogen or a $C_1$ to $C_{10}$ alkyl group, and $R^{22}$, $R^{23}$, and $R^{24}$ are hydrogen, $MX_p$ is chromium(III) chloride, and the organoaluminum compound is an aluminoxane.

A sixteenth embodiment which is the process of the fifteenth embodiment, wherein the oligomer product is formed at (a) an ethylene partial pressure ranging from 150 psig to 2,000 psig (b) a hydrogen partial pressure ranging from 5 psig to 400 psig, (c) a temperature ranging from 20° C. to 150° C., and (d) an aluminum of the aluminoxane to chromium of the 2-[(phosphinyl)aminyl] cyclic imine chromium compound complex molar ratio is in the range of from 10:1 to 5,000:1.

A seventeenth embodiment which is the process of the eleventh through sixteenth embodiments, wherein the oligomer product comprises a liquid oligomer product comprising at least 70 wt. % $C_6$ and/or $C_8$ olefins.

An eighteenth embodiment which is the process of the eleventh through sixteenth embodiments, wherein a liquid oligomer product comprising at least 70 wt. % $C_6$ olefins, and the $C_6$ olefins comprise at least 95 wt. % 1-hexene.

A nineteenth embodiment which is the process of the eleventh through eighteenth embodiments, wherein the process further comprises contacting the 2-[(phosphinyl)aminyl] cyclic imine transition metal compound complex and the organoaluminum compound to form a catalyst system mixture, and aging the catalyst system mixture in the substantial absence of ethylene to form an aged catalyst system mixture.

A twentieth embodiment which is the process of the nineteenth embodiment, wherein the catalyst system is aged in the substantial absence of ethylene for from 5 minutes to 6 hours.

Examples

Preparation of 5-Methoxy-2-methyl-3,4-dihydro-2H-pyrrole

Solid trimethyloxonium tetrafluoroborate (9.9 g, 66.7 mmol, 1.1 equivalent) was added in portions over 30 min to a solution of 5-methylpyrollidinone (6 g, 60.6 mmol, 1 equivalent) in dichloromethane (100 mL). After stirring overnight, the reaction was quenched into 2 M potassium carbonate (500 mL). The mixture was extracted with diethyl ether (5×200 mL) and the combined organic layers were concentrated under a slow stream of nitrogen to give the product as a pale yellow oil (3.7 g, 54% yield). The compound was used as is without further purification.

Preparation of 2-Methyl-3,4-dihydro-2H-pyrrol-5-amine hydrochloride

Solid ammonium chloride (1.57 g, 29.5 mmol, 0.9 equivalents) was added to a solution of 5-methoxy-2-methyl-3,4-dihydro-2H-pyrrol (3.7 g, 32.7 mmol, 1 equivalent) in ethanol (50 mL). After refluxing for 3 hours, the reaction was cooled to room temperature and combined with material from another reaction of equal size. The solvent was removed under reduced pressure. The residue was dissolved in deionized water (20 mL) and washed with ether (50 mL). The aqueous layer was concentrated to dryness and azeotroped with ethanol (2×100 mL). The resulting solid was triturated with methyl tert-butyl ether (20 mL), filtered under a positive stream of nitrogen and dried with nitrogen to give 2-methyl-3,4-dihydro-2H-pyrrol-5-amine hydrochloride (5.4 g, 70% yield) as an off white solid.

Preparation of 2-Methyl-3,4-dihydro-2H-pyrrol-5-[(diisopropylphosphinyl)amine]

In an inert atmosphere glove box, 2-methyl-3,4-dihydro-2H-pyrrol-5-amine hydrochloride (0.500 g, 3.71 mmol) was suspended in tetrahydrofuran (THF) with stirring. To the suspension was added n-butyllithium (7.38 mmol) dropwise over 5 min. This mixture was allowed to stir overnight. To the resulting yellow solution was added chlorodiisopropylphosphine (0.566 g, 3.71 mmol) dropwise with stirring. The resulting mixture was allowed to stir overnight. The solvent was removed in vacuo and the solids were suspended in pentane and diethyl ether then filtered on a frit. The filtrate was dried in vacuo resulting in a white waxy solid. The waxy solid was washed with pentane and then dried in vacuo to provide 2-methyl-3,4-dihydro-2H-pyrrol-5-[(diisopropylphosphinyl)amine] (0.596 g, 2.78 mmol) as a white solid.

Preparation of 2-Methyl-3,4-dihydro-2H-pyrrol-5-[(diisopropylphosphinyl)amine] chromium(III) Chloride Tetrahydrofuran Complex—Complex A In an inert atmosphere glove box, $CrCl_3(THF)_3$ (0.157 g, 419 mmol) was suspended in THF with stirring. To the suspension was added a solution of 2-methyl-3,4-dihydro-2H-pyrrol-5-[(diisopropylphosphinyl)amine] (0.100 g, 467 mmol) in THF dropwise with stirring. The resulting suspension was allowed to stir overnight. From the resultant blue solution, the solvent was removed in vacuo. The resulting solids were stirred in diethyl ether then filtered. The blue solids (0.146 g, 328 mmol) were collected, and subsequently used as Complex A.

Preparation of 6-Methyl-3,4,5,6-tetrahydropyridin-2-amine hydrochloride

2-Amino-6-methylpyridine (10.8 g, 50 mmol) was hydrogenated at 50 psi with rhodium on carbon (5 wt. %, 50% wet, 3.6 g) in 3N hydrochloric acid (500 mL) until hydrogen uptake had ceased. The reaction was filtered through Celite® filter aid and concentrated to dryness under reduced pressure. The residue was concentrated from ethanol (3×100 mL) and then triturated with methyl tert-butyl ether (50 mL). The solids were filtered under a positive stream of nitrogen and dried on the filter under nitrogen for 18 h to give the 6-methyl-3,4,5,6-tetrahydropyridin-2-amine hydrochloride (13.4 g, 90% yield) as an off-white solid.

Preparation of 6-Methyl-3,4,5,6-tetrahydropyridin-2-[(diisopropylphosphinyl)amine]

In an inert atmosphere glove box, 6-methyl-3,4,5,6-tetrahydropyridin-2-amine chloride (0.500 g, 3.36 mmol) was suspended in THF with stirring. To the suspension was added n-butyl lithium (2.75 mL, 6.88 mmol) dropwise over 5 minutes. The resulting yellow solution was allowed to stir for 2 hours. To the solution was added chlorodiisopropylphosphine (0.513 g, 3.36 mmol) dropwise with stirring. The resulting mixture was allowed to stir overnight providing a cloudy solution. The solvent was removed from the cloudy solution in vacuo. The resulting oily material was washed with pentane to provide a white solid. The white solids were dissolved in diethyl ether, filtered, and dried in vacuo to provide 6-methyl-3,4,5,6-tetrahydropyridin-2-[(diisopropylphosphinyl)amine] (0.4 g 1.75 mmol) as a white solid.

Preparation of 6-Methyl-3,4,5,6-tetrahydropyridin-2-[(diisopropylphosphinyl)amine] chromium(III) Chloride Tetrahydrofuran Complex—Complex B In an inert atmosphere glove box, $CrCl_3(THF)_3$ (0.405 g, 1.08 mmol) was suspended in THF with stirring. To the suspension was added a solution of 6-methyl-3,4,5,6-tetrahydropyridin-2-[(diisopropylphosphinyl)amine] (0.260 g, 1.14 mmol) in THF dropwise with stirring. The resulting blue solution was allowed to stir overnight. The solvent was removed in vacuo. The resulting sticky material was stirred in pentane for 30 min and filtered. The isolated solids were then stirred in diethyl ether, filtered, and dried in vacuo. The blue solids (0.450 g, 0.981 mmol) were collected, and subsequently used as Complex B.

Ethylene Oligomerization

The 2-[(phosphinyl)aminyl] cyclic imine compounds and 2-[(phosphinyl)aminyl] cyclic imine transition metal compound complexes were utilized as prepared using the methods described herein. MMAO-3A was obtained from Akzo-Nobel and utilized as obtained from the chemical supplier. The solvents were dried and/or purified using conventional methods and stored under conditions to limit their ability to pick-up water.

General Ethylene Oligomerization Procedure—Runs 1-6

Ethylene oligomerizations were performed using Complex A or Complex B using the following procedure and the amounts and conditions indicated in Table 3.

In a dry box, a 20 mL glass vial was charged with the desired complex, the desired amount of catalyst system solvent, and MMAO-3A (7 wt. % Al solution in heptanes) to provide the desired Al:Cr molar ratio. This solution was then aged for the desired time in the absence of ethylene to provide an aged catalyst system mixture. The aged catalyst system mixture was then added to 0.5 L glass charger containing 200 mL of the oligomerization solvent, cyclohexane.

The glass charger was removed from the dry box and charged into an evacuated 0.5 L stainless steel reactor having an internal temperature of 60° C. Hydrogen was charged to the stainless steel reactor to the desired pressure. Ethylene was then charged to the stainless steel reactor to the desired pressure. The reaction was allowed to proceed at the conditions indicated in Table 1 with ethylene being fed on demand to maintain the desired oligomerization pressure.

At reaction completion, water cooling was applied to the 0.5 L stainless steel reactor using the internal cooling coils. When the stainless steel reactor contents reached 35° C., the unreacted ethylene and hydrogen gas were vented from the stainless steel reactor. A 2 mL sample of the liquid sample was collected, filtered, and analyzed by GC-FID. The stainless steel reactor solids were collected by filtering the liquid solution and cleaning the reactor walls and internal cooling coils. Table 1 provides the analysis of the oligomer product of the ethylene oligomerization and the calculated productivities and activity of the catalyst systems tested in ethylene oligomerization runs 1-6.

TABLE 1

| Ethylene Oligomerization Run # | 1 | 2 | 3 | 4 | 5 | 6 |
|---|---|---|---|---|---|---|
| Catalyst System | | | | | | |
| Complex | A | A | A | A | B | B |
| Mass Complex (mg) | 3.5 | 3.5 | 3.5 | 3.5 | 3.5 | 3.5 |
| mmol complex | 0.0079 | 0.0079 | 0.0079 | 0.0079 | 0.0076 | 0.0076 |
| mg Cr | 0.41 | 0.41 | 0.41 | 0.41 | 0.40 | 0.40 |
| Catalyst System Solvent | EB* | EB | EB | EB | EB | EB |
| Catalyst System Solvent Mass (g) | 1 | 1 | 1 | 1 | 1 | 1 |
| MAO Type | MMAO-3 | MMAO-3 | MMAO-3 | MMAO-3 | MMAO-3 | MMAO-3 |
| Mass MAO (g) | 1.3 | 1.3 | 1.3 | 1.6 | 2.2 | 2.2 |
| Al:Cr ratio | 420 | 420 | 420 | 530 | 750 | 750 |
| Catalyst System Aging Time (hours) | 1 | 1 | 4 | 1 | 0.5 | 0.5 |
| Ethylene Oligomerization Conditions | | | | | | |
| Organic Reaction Medium | Cy** | Cy | Cy | Cy | Cy | Cy |
| Organic Reaction Medium Volume (mL) | 200 | 200 | 200 | 200 | 200 | 200 |
| Ethylene Pressure (psi) | 875 | 875 | 875 | 875 | 875 | 875 |
| Hydrogen Pressure (psi) | 50 | 50 | 50 | 50 | 50 | 50 |
| Oligomerization Temperature (° C.) | 70 | 70 | 70 | 70 | 70 | 80 |
| Oligomerization Time (minutes) | 20 | 45 | 20 | 45 | 20 | 20 |

TABLE 1-continued

| Ethylene Oligomerization Run # | 1 | 2 | 3 | 4 | 5 | 6 |
|---|---|---|---|---|---|---|
| Oligomer Product | | | | | | |
| Polymer (grams) | 0.0001 | 0.04 | 0.0001 | 0.28 | 0.04 | 0.02 |
| Liquid Oligomer Product (grams) | 29 | 75 | 10 | 75 | 102 | 86 |
| Polymer (wt. %) | 0.00 | 0.05 | 0.00 | 0.37 | 0.04 | 0.02 |
| Liquid Oligomer Product Distribution | | | | | | |
| $C_6$ (wt. %) | 74.5 | 82.4 | 90.2 | 80.2 | 90.4 | 91.8 |
| 1-hexene (wt. % of $C_6$ product) | 92.51 | 95.81 | 97.61 | 94.96 | 96.67 | 97.28 |
| Methylcyclopentane (wt. % of $C_6$ product) | 3.00 | 1.59 | 0.98 | 1.91 | 1.33 | 1.04 |
| Methylenecyclopentane (wt. % of $C_6$ product) | 3.98 | 2.13 | 0.95 | 2.58 | 1.57 | 1.24 |
| $C_8$ (wt. %) | 23.5 | 14.9 | 8.4 | 17.1 | 7.1 | 5.7 |
| 1-octene (wt. % of $C_8$ product) | 96.89 | 96.78 | 97.43 | 99.70 | 98.33 | 97.79 |
| $C_{10}$ (wt. %) | 1.4 | 2.0 | 1.2 | 2.1 | 2.2 | 2.2 |
| $C_{12}$ (wt. %) | 0.6 | 0.6 | 0.3 | 0.7 | 0.2 | 0.3 |
| $C_{14+}$ (wt. %) | 0.0 | 0.0 | 0.0 | 0.0 | 0 | 0 |
| Total C6 + C8 (wt. %) | 98.0 | 97.4 | 98.6 | 97.2 | 97.6 | 97.6 |
| Ethylene Oligomerization Productivities and Activities | | | | | | |
| Grams ($C_6$ + $C_8$)/gram Cr | 68,714 | 178,839 | 23,345 | 177,587 | 250,552 | 211,606 |
| Grams ($C_6$ + $C_8$)/gram Cr/hour | 206,142 | 238,452 | 70,036 | 236,783 | 751,655 | 634,819 |

*EB = ethylbenzene
**Cy = cyclohexane

The invention illustratively disclosed herein suitably can be practiced in the absence of any element that is not specifically disclosed herein and/or any optional element disclosed herein. While compositions and processes are described in terms of "comprising," "containing," or "including" various components or steps, the compositions and processes can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims below.

What is claimed is:

1. A catalyst system comprising
i) a 2-[(phosphinyl)aminyl] cyclic imine transition metal compound complex having the structure;

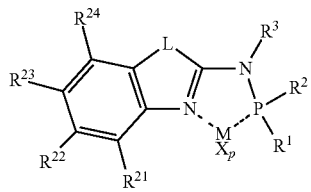

wherein:

$R^1$ and $R^2$ are each independently a $C_1$ to $C_{20}$ organyl group consisting essentially of inert functional groups, wherein each inert functional group independently is a halo group, a nitro group, a hydrocarboxy group, a sulfidyl group, or a hydrocarbyl group, $R^3$ is hydrogen or a $C_1$ to $C_{20}$ organyl group, L is —(CrR")$_m$— where each R' and R" independently is a hydrogen or a $C_1$ to $C_{10}$ organyl group consisting essentially of inert functional groups, wherein each inert functional group independently is a halo group, a nitro group, a hydrocarboxy group, a sulfidyl group, or a hydrocarbyl group, and m is 1, 2, or 3, $R^{21}$, $R^{22}$, $R^{23}$, and $R^{24}$ are each independently hydrogen or a $C_1$ to $C_{20}$ organyl group consisting essentially of inert functional groups, wherein each inert functional group independently is halo group, a nitro group, a hydrocarboxy group, a sulfidyl group, or a hydrocarbyl group, and $MX_p$ represents a transition metal compound where M is a transition metal, X is a monoanion, p ranges from 2 to 6, and each X independently is a halide, a carboxylate, a β-diketonate, a hydrocarboxide, a nitrate, or a chlorate; and ii) an organoaluminum compound.

2. The catalyst system of claim 1, wherein

L is —(CH$_2$)$_m$— where m is 1, 2, or 3,

R$^{21}$ is hydrogen or a C$_1$ to C$_{10}$ alkyl group, and R$^{22}$, R$^{23}$, and R$^{24}$ are hydrogen.

3. The catalyst system of claim 1, wherein R$^3$ is hydrogen.

4. The catalyst system of claim 1, wherein the transition metal compound comprises a chromium(III) carboxylate, a chromium(III) β-diketonate, or a chromium(III) halide.

5. The catalyst system of claim 1, wherein the organoaluminum compound comprises an aluminoxane.

6. The catalyst system of claim 5, wherein the aluminoxane comprises methylaluminoxane, modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

7. The catalyst system of claim 5, wherein the aluminoxane comprises modified methylaluminoxane.

8. The catalyst system of claim 5, wherein an aluminum of the aluminoxane to transition metal of the 2-[(phosphinyl) aminyl] cyclic imine transition metal compound complex molar ratio is in the range of from 10:1 to 5,000:1.

9. The catalyst system of claim 1, wherein the 2-[(phosphinyl)aminyl] cyclic imine transition metal compound complex has the structure:

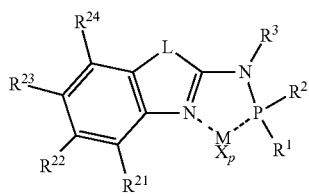

wherein:

R$^1$ and R$^2$ are each independently a C$_1$ to C$_{20}$ organyl group consisting essentially of inert functional groups, wherein each inert functional group independently is a halo group, a nitro group, a hydrocarboxy group, a sulfidyl group, or a hydrocarbyl group, R$^3$ is hydrogen, L is —(CH$_2$)$_m$— where m is 1, 2, or 3, R$^{21}$ is hydrogen or a C$_1$ to C$_{10}$ alkyl group, and R$^{22}$, R$^{23}$, and R$^{24}$ are hydrogen, MX$_p$ is chromium(III) chloride, the organoaluminum compound is an aluminoxane, and an aluminum of the aluminoxane to chromium of the 2-[(phosphinyl)aminyl] cyclic imine chromium compound complex molar ratio is in the range of from 10:1 to 5,000:1.

10. A process comprising:

contacting i) ethylene, ii) a catalyst system comprising (a) a 2-[(phosphinyl)aminyl] cyclic imine transition metal compound complex having the structure,

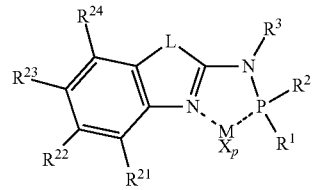

wherein:

R$^1$ and R$^2$ are each independently a C$_1$ to C$_{20}$ organyl group consisting essentially of inert functional groups, wherein each inert functional group independently is a halo group, a nitro group, a hydrocarboxy group, a sulfidyl group, or a hydrocarbyl group, R$^3$ is hydrogen or a C$_1$ to C$_{20}$ organyl group, L is —(CR'R")$_m$— where each R' and R" independently is a hydrogen or a C$_1$ to C$_{10}$ organyl group consisting essentially of inert functional groups, wherein each inert functional group independently is a halo group, a nitro group, a hydrocarboxy group, a sulfidyl group, or a hydrocarbyl group, and m is 1, 2, or 3, R$^{21}$, R$^{22}$, R$^{23}$, and R$^{24}$, are each independently hydrogen or a C$_1$ to C$_{20}$ organyl group consisting essentially of inert functional groups, wherein each inert functional group independently is a halo group, a nitro group, a hydrocarboxy group, a sulfidyl group, or a hydrocarbyl group, and MX$_p$ represents a transition metal compound where M is a transition metal, X is a monoanion, p ranges from 2 to 6, and each X independently is a halide, a carboxylate, a β-diketonnate, a hydrocarboxide, a nitrate, or a chlorate; and (b) an organoaluminum compound, and iii) optionally hydrogen to form an oligomer product.

11. The process of claim 10, wherein the transition metal compound comprises a chromium(III) carboxylate, a chromium(III) β-diketonate, or a chromium(III) halide.

12. The process of claim 10, wherein the organoaluminum compound comprises an aluminoxane.

13. The process of claim 10, wherein the 2-[(phosphinyl)aminyl] cyclic imine transition metal compound complex has the general structure:

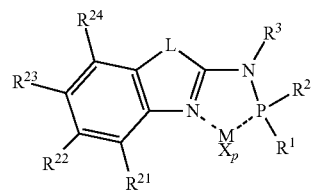

wherein:

R$^1$ and R$^2$ are each independently a C$_1$ to C$_{20}$ organyl group consisting essentially of inert functional groups, wherein each inert functional group independently is a halo group, a nitro group, a hydrocarboxy group, a sulfidyl group, or a hydrocarbyl group, R$^3$ is hydrogen, L is —(CH$_2$)$_m$— where m is 1, 2, or 3, $R^{21}$ is hydrogen or a $C_1$ to $C_{10}$ alkyl group, and $R^{22}$, $R^{23}$, and $R^{24}$ are hydrogen, $MX_p$ is chromium(III) chloride, and the organoaluminum compound is an aluminoxane.

14. The process of claim 13, wherein the oligomer product is formed at
    (a) an ethylene partial pressure ranging from 150 psig to 2,000 psig,
    (b) a hydrogen partial pressure ranging from 5 psig to 400 psig,
    (c) a temperature ranging from 20° C. to 150° C., and
    (d) an aluminum of the aluminoxane to chromium of the 2-[(phosphinyl)aminyl] cyclic imine chromium compound complex molar ratio is in the range of from 10:1 to 5,000:1.

15. The process of claim 14, wherein the oligomer product comprises a liquid oligomer product comprising equal to or greater than 70 wt. % $C_6$ and/or $C_8$ olefins.

16. The process of claim 15, wherein the $C_6$ olefins comprise at least 95 wt. % 1-hexene.

17. The process of claim 10, wherein the process further comprises contacting the 2-[(phosphinyl)aminyl] cyclic imine transition metal compound complex and the organoaluminum compound to form a catalyst system mixture, and aging the catalyst system mixture in the substantial absence of ethylene to form an aged catalyst system mixture.

18. The process of claim 17, wherein the catalyst system is aged in the substantial absence of ethylene for from 5 minutes to 6 hours.

* * * * *